US007735652B2

(12) United States Patent
Inglis et al.

(10) Patent No.: US 7,735,652 B2
(45) Date of Patent: Jun. 15, 2010

(54) APPARATUS AND METHOD FOR CONTINUOUS PARTICLE SEPARATION

(75) Inventors: David William Inglis, Marsfield (AU); John Davis, Staten Island, NY (US); Robert Austin, Princeton, NJ (US); James Sturm, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 406 days.

(21) Appl. No.: 11/809,559

(22) Filed: May 31, 2007

(65) Prior Publication Data

US 2008/0023399 A1    Jan. 31, 2008

Related U.S. Application Data

(60) Provisional application No. 60/809,933, filed on Jun. 1, 2006.

(51) Int. Cl.
*B03B 5/00* (2006.01)
*B01D 37/00* (2006.01)

(52) U.S. Cl. ............... 209/155; 210/767; 210/433.1

(58) Field of Classification Search ............ 209/155, 209/208; 204/451; 210/767
See application file for complete search history.

(56) References Cited

U.S. PATENT DOCUMENTS 5,427,663 A    6/1995   Austin et al.
5,707,799 A *  1/1998   Hansmann et al. ............. 435/6
6,432,630 B1 * 8/2002   Blankenstein .................. 435/4
7,150,812 B2 * 12/2006  Huang et al. ................. 204/451
7,157,274 B2 * 1/2007   Bohm et al. .................. 435/325
7,276,170 B2 * 10/2007  Oakey et al. ................. 210/767
2006/0118479 A1 * 6/2006 Shevkoplyas et al. .... 210/433.1

OTHER PUBLICATIONS

J. Calvin Giddings, "Field-Flow Fractionation: Analysis of Macromolecular, Colloidal, and Particulate Materials", Science 260: 1456-1465, 1993.
J. Calvin Giddings, "'Eddy' Diffusion in Chromatography", Nature 184, pp. 357, 1959.
Chou et al., "Sorting by Diffusion: An Asymmetric Obstacle Course for Continuous Molecular Separation", Proc. Natl. Acad. Sci. 96(24): 13762-13765, 1999.
Han et al., "Separation of Long DNA Molecules in a Microfabricated Entropic Trap Array", Science 288: 1026-1029, 2000.
Huang et al., "A DNA Prism for High-Speed Continuous Fractionation of Large DNA Molecules", Nat Biotechnol. 20: 1048-1051, 2002.
Turner et al., "Confinement-Induced Entropic Recoil of Single DNA Molecules in a Nanofluidic Structure", Phys. Rev. Lett. 88(12): 128103-1-128103-4, 2002.
Huang et al., "Role Molecular Size in Ratchet Fractionation", Phys. Rev. Lett. 89(17): 178301-1-178301-4, 2002.

(Continued)

*Primary Examiner*—Patrick H Mackey
*Assistant Examiner*—Terrell H Matthews
(74) *Attorney, Agent, or Firm*—Kenyon & Kenyon LLP (57) ABSTRACT

The invention is directed to an apparatus and a method of separating particles, such as cells, from a heterogeneous fluid, such as blood, where the particles have a large range of sizes.

18 Claims, 7 Drawing Sheets

OTHER PUBLICATIONS

Huang et al., "Tilted Brownian Ratchet for DNA Analysis", Anal. Chem. 75(24): 6963-6967, 2003.

Savel'ev et al., "Separating Particle According to Their Physical Properties: Transverse Drift of Underdamped and Overdamped Interacting Particles Diffusing Through Two-Dimensional Ratchets", Phys. Rev. B 71: 214303-1-214303-11, 2005.

Li et al., "Separation of Suspended Particles by Array of Obstacles in Microfluidic Devices", Phys. Rev. Lett. 98: 050602-1-050602-4, 2007.

Inglis et al., "Continuous Microfluidic Immunomagnetic Cell Separation", Appl. Phys. Let. 85(21): 5093-5095, 2004.

Li et al., "Dielectrophoretic Fluidic Cell Fractionation System", Anal. Chimica Acta 507: 151-161, 2004.

Fu et al., "A Patterned Anisotropic Nanofluidic Sieving Structure for Continuous-Flow Separation of DNA and Proteins", Nature Nanotechnology 2:121-128, 2007.

Pelton et al., "Transport and Fractionation in Periodic Potential-Energy Landscapes", Phys. Rev. E 70, 031108-1-031108-10, 2004.

Huang et al., "Continuous Particle Separation Through Deterministic Lateral Displacement", Science 304: 987-990, 2004.

International Search Report dated Sep. 24, 2008, International Application No. PCT/US2007/013130.

Written Opinion dated Sep. 24, 2008, International Application No. PCT/US2007/013130.

\* cited by examiner

Figure 7

APPARATUS AND METHOD FOR CONTINUOUS PARTICLE SEPARATION

This application claims benefit of provisional application Ser. No. 60/809,933, filed Jun. 1, 2006, the contents of which are incorporated herein by reference in their entirety.

FIELD OF THE INVENTION

The present invention relates to methods and devices for separating particles according to size. More specifically, the present invention relates to a microfluidic method and device for the separation of particles according to size.

BACKGROUND

Separation by size or mass is a fundamental analytical and preparative technique in biology, medicine, chemistry, and industry. Conventional methods include gel electrophoresis, field-flow fractionation, sedimentation and size exclusion chromatography [J. C. Giddings, Unified Separation Science (Wiley, New York, 1991)]. Gel electrophoresis utilizes an electric field to drive charged molecules to be separated through a gel medium, which serves as a sieving matrix. The molecules are initially loaded at one end of a gel matrix, and are separated into component zones as they migrate through the gel. Field-flow fractionation is carried out in a thin ribbon-like channel, in which the flow profile is parabolic. Particles are loaded as a sample zone, and then flow through the channel. Separation occurs as particles of different properties flow in different positions of the flow, due to the influence of a field, resulting in different migration speeds. The field is applied perpendicular to the flow. Sedimentation utilizes gravitational or centrifugal acceleration to force particles through a fluid. Particles migrate through the fluid at different speeds, depending on their sizes and densities, and thus are separated. Size exclusion chromatography (SEC) utilizes a tube packed with porous beads, through which sample molecules are washed. Molecules smaller than the pores can enter the beads, which lengthen their migration path, whereas those larger than the pores can only flow between the beads. In this way smaller molecules are on average retained longer and thus become separated from larger molecules. Zones broaden, however, as they pass through the column, because there are many possible migration paths for each molecule and each path has a different length, and consequently a different retention time. This multipath zone broadening (Eddy diffusion) is a major factor limiting resolution. J. C. Giddings, *Unified Separation Science* (John Wiley & Sons, New York, 1991). Other methods for separation according to size, including gel electrophoresis, field-flow fractionation, also involve stochastic processes, which may limit their resolution. J. C. Giddings, *Nature* 184, 357 (1959); J. C. Giddings, *Science* 260, 1456 (1993).

The need for reliable and fast separation of large biomolecules such as DNA and proteins cannot be overemphasized. Recently, micro/nano-fabricated structures exploiting various ideas for DNA separation have been demonstrated. The use of micro/nano-fabricated structures as sieving matrices for particle separation was disclosed in U.S. Pat. No. 5,427,663. According to this document, DNA molecules are separated as they are driven by electric fields through an array of posts. U.S. Pat. No. 5,427,663 discloses a sorting apparatus and method for fractionating and simultaneously viewing individual microstructures and macromolecules, including nucleic acids and proteins. According to U.S. Pat. No. 5,427,663, a substrate having a shallow receptacle located on a side thereof is provided, and an array of obstacles outstanding from the floor of the receptacles is provided to interact with the microstructures and retard the migration thereof. To create migration of the microstructures, electrodes for generating electric fields in the fluid are made on two sides of the receptacle. This is analogous to the conventional gel electrophoresis. However, micro-machined structures are substituted for gel as sieving matrices.

A variety of micro-fabricated sieving matrices have been disclosed. In one design, arrays of obstacles sort DNA molecules according to their diffusion coefficients using an applied electric field [Chou, C. F. et. al, *Proc. Natl. Acad. Sci.* 96, 13762 (1999).]. The electric field propels the molecules directly through the gaps between obstacles, wherein each gap is directly below another gap. The obstacles are shaped so that diffusion is biased in one direction as DNA flows through the array. After flowing through many rows of obstacles, DNA with different diffusion coefficients are deflected to different positions. However, because the diffusion coefficient is low for large molecules, the asymmetric obstacle arrays are slow, with running times of typically more than 2 hours. In a second design, entropic traps consisting of a series of many narrow constrictions (<100 nm) separated by wider and deeper regions (a few microns), reduce the separation time to about 30 minutes [Han, J. & Craighead, H. G., *Science* 288, 1026 (2000).]. Because the constrictions are fabricated to be narrower than the radius of gyration of DNA molecules to be separated, they act as entropic barriers. The probability of a molecule overcoming the entropic barrier is dependent on molecular weight, and thus DNA molecules migrate in the entropic trap array with different mobilities. Larger molecules, with more degrees of configurational freedom, migrate faster in these devices. In a third design, a hexagonal array of posts acts as the sieving matrix in pulsed-field electrophoresis for separation of DNA molecules in the 100 kb range [Huang, L. R., Tegenfeldt, J. O., Kraeft, J. J., Sturm, J. C., Austin, R. H. and Cox, E. C., *Nat Biotechnol.* 20, 1048 (2002).]. However, these devices generally require features sizes comparable to or smaller than the molecules being fractionated. Han, J. & Craighead, H. G. Separation of long DNA molecules in a micro-fabricated entropic trap array. *Science* 288, 1026-1029 (2000); Turner, S. W., Cabodi, M., Craighead, H. G. Confinement-induced entropic recoil of single DNA molecules in a nanofluidic structure. *Phys Rev Lett.* 2002 Mar. 25; 88(12):128103; Huang, L. R., Tegenfeldt, J. O., Kraeft, J. J., Sturm, J. C., Austin, R. H. and Cox, E. C. A DNA prism for high-speed continuous fractionation of large DNA molecules. *Nat Biotechnol.* 2002 October; 20(10):1048-51; and Huang, L. R., Silberzan, P., Tegenfeldt, J. O., Cox, E. C., Sturm, J. C., Austin, R. H. and Craighead, H. Role of molecular size in ratchet fractionation. *Phys. Rev. Lett.* 89, 178301 (2002). The need for small feature size may have the following detrimental effects: (i) the devices cannot fractionate small molecules such as proteins, (ii) the devices may have very low throughput, and thus are not useful sample preparation tools, (iii) the devices can only analyze very small volume of samples, and therefore usually require concentrated samples or expensive equipment for sample detection, and (iv) manufacturing the devices require state-of-the-art fabrication techniques, and thus high cost.

Human blood is a highly complex fluid containing objects of many different sizes and shapes. Blood plasma is the cell-free, clear, straw-colored fluid, which is free of objects bigger than 0.5 μm. The cell component consists of three main classes: (i) leukocytes or white blood cells (WBCs) are parts of the immune system, are roughly spherical, and range from 5 to 20 μm in diameter; (ii) erythrocytes or red blood cells (RBCs), carry oxygen to the tissue and are biconcave and discoidal (8 μm in diameter and 2 μm thick); and (iii) platelets range from 1 to 3 μm in diameter and are responsible for the clotting reaction (1, 2). Plasma, containing salts and proteins, constitutes a little over half the volume of blood. The rest of the volume is made up of cells. Over 90 percent of the cells are red blood cells.

Traditionally, the components of blood may be fractionated according to various physical properties, including buoyant density (3) and electric charge (4), and by specific immunologic methods (5). In some of these approaches, fluorescent or magnetic particles are selectively attached to components in blood through an immunologic target. Magnetic cell sorting (MACS) and flow cytometry (FACS) are widely used methods. However, they typically require additional labels. Size, without labels, has also been used to isolate rare blood components by using filter-based methods (6). The removed component may be harvested by periodically stopping the flow into the filter and flushing to remove the desired particles from the filter mesh. Additional microfluidic methods have also included magnetophoretic separation (7) and separation by leukocyte margination (8). Size-based filter methods have also been integrated with PCR amplification of genomic DNA from WBCs (9). In general, these processes are complex, involve fluorescent labeling, yield incomplete fractionation, clog easily, or introduce bias to the data.

U.S. Pat. No. 7,150,812, which claims priority to provisional application Ser. No. 60/420,756, filed Oct. 23, 2002, the contents of which are incorporated herein by reference in their entirety, discloses a microfluidic device for separating particles according to size and a method of separating particles with the disclosed device. The device comprises a microfluidic channel, and an array comprising a network of gaps within the microfluidic channel. The device employs a field that propels the particles being separated through the microfluidic channel. The individual field flux exiting a gap is divided unequally into a major flux component and a minor flux component into subsequent gaps in the array, such that the average direction of the major flux components is not parallel to the average direction of the field. The disclosed method comprises introducing the particles to be separated into an array comprising a network of gaps within the microfluidic channel and applying a field to the particles to propel the particles through the array. A field flux from the gaps is divided unequally into a major flux component and a minor flux component into subsequent gaps in the array, such that the average direction of the major flux components is not parallel to the average direction of the field. Preferably, the array is an ordered array of obstacles that is asymmetric with respect to the average direction of the applied field.

When particles having a large size range, such as the cells found in blood, are separated according to size in any of those prior art devices, multiple devices, either cascaded or in series, are required to prevent clogging. Therefore, a need exists for a single separation device that can separate blood cells in a blood sample or particles having a similar size range in other fluid samples and a method for separating particles having such a size range in a fluid sample that does not require complex off-device fluid handling. The present invention provides such a device and method.

SUMMARY OF THE INVENTION

The invention is directed to a continuous flow fluidic particle separation device. Preferably, the device comprises a sample input, a carrier fluid input, and a plurality of separation areas in fluid connection with the sample input. The separation areas are adapted to separate particles having a size equal to or greater than a critical size from particles having a size less than the critical size in a fluid sample, where the critical size for each separation area is different, and particles having a size less than the critical size and particles having at least the critical size in a separation area move in different directions. The device further comprises at least one non-clogging pathway in fluid connection with the carrier fluid input, adapted to accept separated particles from at least one of the separation areas, a sample output in fluid connection with the separation areas, and at least one alternate output in fluid connection with the non-clogging pathway, where, when a heterogeneous fluid sample containing particles to be separated by size is introduced into the device through the sample input, and a carrier fluid is introduced into the device through the carrier fluid input, the fluid sample passes through the separation areas, the carrier fluid passes through the non-clogging pathway in contact with the fluid sample in the separation areas, no mixing other than diffusion occurs between the liquids, and particles separated in the separation areas pass into the carrier fluid.

The invention is also directed to a method of separating particles by size in a continuous fluid flow. The method comprises introducing a heterogeneous fluid sample into a sample input of a continuous flow fluidic particle separation device, and a carrier fluid into a carrier fluid input of the device, thereby providing a sample flow through a plurality of separation areas and a carrier flow parallel to and in contact with the sample flow, wherein each of the flows has a sufficiently low Reynolds number that there substantially no turbulence, and mixing of the fluids in the flow occurs only through diffusion, separating particles having a size at least that of a predetermined critical size from particles having a size less than the critical size, where each separation area has a different critical size, and passing the separated particles into the carrier fluid

BRIEF DESCRIPTION OF THE DRAWINGS

FIG. 1 is a schematic illustrating separation by deterministic lateral displacement in an array of micro-posts, with an example row shift fraction of one third. This shift creates three equal flux streamlines. The dashed lines are the boundaries between the streamlines, which are assigned an index in the gaps between the posts. Paths of particles both smaller and larger than the critical threshold are depicted with dotted lines extending from the indicated particles. Small particles stay within a flow stream, and large particles are displaced at each obstacle. G is the clear spacing in gaps between the microposts, λ is the center-to-center post separation, and d is the relative shift of the post centers in adjacent rows.

FIG. 2B illustrates the predicted input-output curve for the FD, where hard sphere diameters are graphed as a function of displacement from the left wall with the lateral position of the blood injection point at the top of the device indicated by the arrow. The positions of the three exit channels used to collect the fractionated blood and buffer samples are also indicated.

In FIG. 5A, the fluid flow is not vertical, fluid moves to the low resistance area when possible. In FIG. 5B, additional fluid is supplied to the low resistance area, preventing lateral flow.

DETAILED DESCRIPTION OF THE PREFERRED EMBODIMENTS

The present invention is directed to devices and methods for separating particles suspended in liquids. Preferably, the present invention provides devices and methods for separating particles having a relatively large size range. Separation devices and methods of the invention preferably can be used to separate particles having a size range of from less than 1 µm to greater than 10 µm, and, more preferably, from less than 1 µm to greater than 20 µm. Preferably, the devices of the invention may be used to separate the components of blood, including plasma, white blood cells, red blood cells, and plasma. However, the devices and methods of the invention may be used to separate particles from any fluid having characteristics relatively similar to blood, such as other biological fluids. The device of the invention may be used to separate bacteria, cells, organelles, viruses, nucleic acids (i.e., DNA, etc.), proteins, and protein complexes, as well as non-biological particles suspended in fluid, such as industrial polymers, powders, latexes, emulsions, and colloids.

As used herein, the terms "carrier fluid" and "buffer" refer to any particle free fluid that is a suitable medium for the particles being separated. A carrier fluid or buffer preferably used for the separation of blood is a phosphate buffered saline. Carrier fluids and buffers may also contain additives. Additives that prevent adhesion include Bovine Serum Albumin (BSA) and F108, a surfactant manufactured by BASF. Anticoagulant additives, such as EDTA, may also be used.

The present invention is described herein in terms of the separation arrays of the microfluidic devices disclosed in U.S. Pat. No. 7,150,812. However, as will be recognized by those skilled in the art, any other type of microfluidic device that separates particles by size by displacing separated particles at an angle to the flow through the device can be used with the present invention. Such devices include, but are not limited to Brownian ratchet arrays, such as those disclosed by Huang et al., Anal. Chem. 75, 6963-6967 (2003), Savel'ev et al., Phys. Rev. B 71, 214303 (2005), and Li et al., Phys. Rev. Let. 98, 050602 (2007), in which Brownian motion or diffusion is enhanced in one direction and limited in the opposite direction by the particle's interactions with micro-fabricated structures, where the amount of Brownian motion experienced by a particle is inversely proportional to its size; devices utilizing high gradient magnetic separation over micro-fabricated ferromagnetic stripes, such as those disclosed by Inglis et al., Appl. Phys. Let. 85, 5093-5095 (2004), and dielectrophoretic separation using micro-fabricated stripes, such as those disclose by Li et al., Analytica Chimica Acta 507, 151-161 (2004), in which the force of attraction is highest when the features are of similar size to the particles being separated, and channel height must also be similar to particle size for efficient separation; anisotropic sieving structures, such as those disclosed by Fu et al., Nature Nanotechnology 2, 121-128 (2007), that continuously sort macromolecules; and other devices that perform separations by flowing particles at non-tangential angles to periodic potentials, such as those disclosed by Pelton et al., Phys. Rev. E 70, 031108 (2004), the contents of which are incorporated herein by reference in their entirety.

U.S. Pat. No. 7,150,812 and L. R. Huang et al., CONTINUOUS PARTICLE SEPARATION THROUGH DETERMINISTIC LATERAL DISPLACEMENT, Science, 304, 987-990 (2004), the contents of which are incorporated herein by reference in their entirety, disclose the basic separation principles of deterministic lateral displacement, a process that may also be referred to as "bumping." Huang et al. disclosed a microfluidic device that was used to separate 0.6 to 1.0 µm polystyrene particles with a 10 nm size resolution. In the disclosed device, fluid flows through an array of obstacles, such as micro-posts, in which each row of posts is slightly offset laterally with respect to the previous row above it. In the present invention, the array is preferably an ordered array, and, more preferably, is an ordered array of micro- or nano-fabricated features, such as micro-posts.

Figure 1:
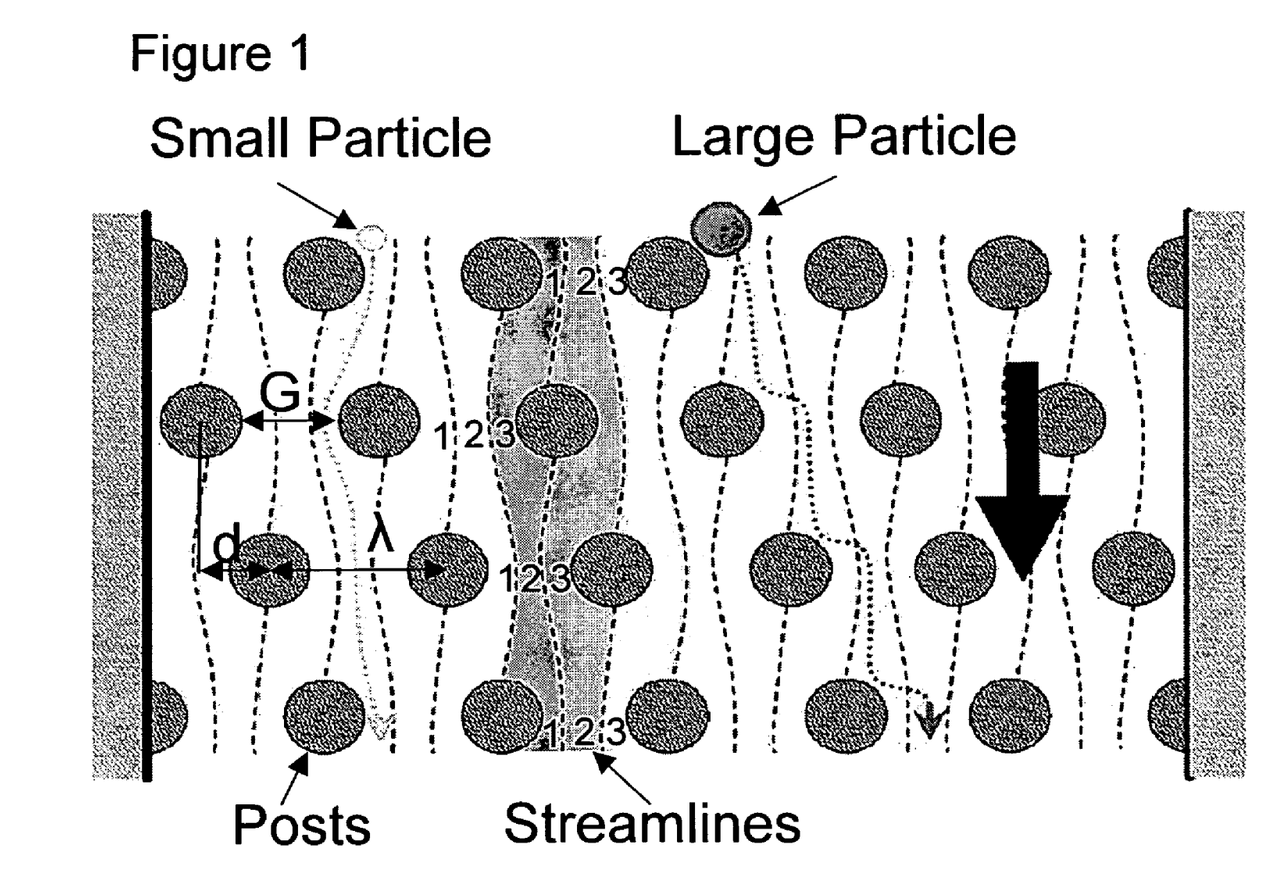

FIG. 1 illustrates separation of particles by deterministic lateral displacement, i.e., "bumping," in an array of micro-posts. As illustrated in FIG. 1, each row has a row shift fraction of one third, which creates three equal flux streamlines, where the dashed lines are the boundaries between the streamlines, which are indexed in the gaps between the posts. Paths of particles both smaller and larger than the critical threshold are depicted with dotted lines extending from the indicated particles. Small particles stay within a flow stream and large particles are displaced at each obstacle. G is the clear spacing between the gap, λ is the center-to-center post separation, and d is the relative shift of the post centers in adjacent rows.

In the array, particles below a critical size, $D_c$, follow streamlines cyclically through the gaps, moving in an average downward flow direction. That is, particles having a size less than the critical size, $D_c$, have the same direction of travel as the flow on average. In contrast, particles having a size of at least the critical size, $D_c$, i.e., particles having a size at least that of a critical threshold size, do not fit into the first streamline, and are moved by hydrodynamic lateral drag, i.e., are "bumped," into the sequential streamline at each post. Thus, they do not move parallel to the fluid flow, but, instead, at an angle determined by the ratio of post offset to row-to-row spacing. The critical size, $D_c$, is twice the width of the first streamline adjacent to the post in the gap of FIG. 1, so that the centers of particles having a size at least that of the critical size are bumped into the second stream line.

If the center-to-center spacing the posts is $\lambda$ and the relative shift between the adjacent post rows is d, then the parameter $\epsilon$ is a measure of both the relative shift and the tangent of the angle with respect to the vertical at which bumped objects move through the array.

$$\varepsilon = \frac{d}{\lambda} \quad (1)$$

In general, a smaller $\epsilon$ results in an array with a smaller critical size. The critical size, $D_c$, can easily be designed to be a quarter to a third the gap, G, between the posts. Thus, large particles that are several times larger than the critical size are not trapped, as in a filter, and the array does not easily clog at high flow rates or large particle densities. However, in a highly heterogeneous liquid, such as blood, where particle sizes differ by more than a factor of ten, a simple variation in $\epsilon$ is not sufficient to fractionate all of the components of interest. Additional design variations are required to expand the range of particle sizes that can be separated to create a non-clogging device.

A bump array, unlike many other separation technologies, utilizes a deterministic process, rather than a stochastic process such as diffusion. As a result, faster flow rates produce less diffusional mixing of components, and the performance of the device improves with increasing speed. Two dimensionless variables are useful in the analysis of the movement of liquids in the device of the invention: the Reynolds number, $R_e$, of the fluid flow and the Peclet number, $P_e$, of the particles transported by the fluid within the device. The Reynolds number may be approximated by $$R_e \approx \frac{\rho v S}{\eta}, \quad (2)$$

and the Peclet number may be approximated by $$P_e \approx \frac{v \varepsilon L}{D}, \quad (3)$$

where $\rho$ is the density of the fluid, $v$ is the local speed of the fluid, S is a characteristic length over which the fluid changes its direction, $\eta$ is the viscosity of the fluid, $\epsilon L$ is a characteristic length over which diffusion competes with fluid transport, i.e., advection, about $\epsilon\lambda$ at the local scale of the posts, and D is the diffusion coefficient of particles of radius a in the flow that are separated from the flow streamlines in the bumping process. For a simple spherical object:

$$D = \frac{k_B T}{6\pi \eta a}, \quad (4)$$

where $k_B T$ is the thermal energy at temperature T. If $R_e$ is less than 1, the viscous damping caused by shear quickly removes translational and rotational kinetic energy from a fluid element, and the flow is laminar with no turbulence. If $P_e$ is greater than 1, the diffusion rate is smaller than the advection rate between rows of posts, and the flow is "deterministic" in that small particles are basically confined to streamlines, and particles having a size at least that of the critical size of the array are "bumped."

In the present invention, the maximum flow rates to those rates where $R_e<1$. In experiments with the present invention, $v \leq 0.1$ cm/s and $l \approx 10^{-3}$ cm yield $R_e \leq 10^{-2}$. Thus, flow rates of greater than 10 cm/sec are possible in the present invention, while maintaining the flow in a low $R_e$ regime.

The Peclet number, $P_e$, does not have an absolute value for a given blood flow velocity, as $P_e$ is a function of particle size. In addition, there are two different size scales for diffusion in the device of the invention. Diffusion on the local scale of the posts moves particles out of the streamlines, and can ruin the deterministic bumping process. Diffusion on the scale of the total array length size scale, Z, broadens the lines of separated objects, and can ruin resolution even in the presence of successful bumping.

For diffusion that occurs between streamlines, while traveling the distance of a row-to-row spacing, $\lambda$, a particle can diffuse into a different streamline a distance $\epsilon\lambda$ away, separation of the particle by "bumping" will be compromised. For the separation of blood platelets having a radius, R, $\approx 1\times 10^{-4}$ cm, a device of the invention having a minimum value of $\epsilon$ of 0.04, a minimum value of $\lambda$ of $5\times 10^{-4}$ cm, an operational speed, v, of 0.1 cm/sec, demonstrates that platelets have a $P_e$ on the order of $1\times 10^3$, allowing the diffusion of all blood cells to be safely ignored. In contrast, proteins, which are approximately 5 nm in radius, in the blood plasma will have a $P_e$ of roughly 2. Although the proteins are under the critical size, and, thus, will not bump, diffusion will broaden the distribution of the proteins as they move through the array.

The overall lateral diffusion of small particles along the complete length, Z, of the device is particularly important for the analysis of proteins and ions, because diffusion broadening may result in the loss of plasma proteins into the area where the cells are "bumped." Diffusion broadening along the length of the device can be computed simply from $x^2=2DZ/v$. For a complete device having a length of about 4 cm at speed of 0.1 cm/sec, a protein will diffuse a distance laterally of about $10^{-2}$ cm, i.e., about 100 µm, and ions will diffuse a distance of about $10^{-1}$ cm, i.e., about 1,000 µm. This broadening sets a limit to the purity of the "unbumped" material.

The rotation of non-spherical objects as they move through the arrays used in the invention and/or the distortion of deformable shapes caused by shear can also be important in separations. The shearing torques are due to the local curl of the vector velocity field near surfaces, and the net force fields are due to high pressure gradients as a fluid is forced through the a gap. The shearing torques and hydrostatic force fields can not only rotate and deform the cells, have been known to lyse the cells if the shearing torques and hydrostatic pressure gradients become too high. The spatial dependence of the vector velocity field can be computed in a straightforward manner, as the fluid flow is laminar. However, the calculation of the shear fields and hydrostatic forces acting on non-spherical objects is quite difficult, because large objects substantially disturb the flow fields. The hydrostatic pressure gradients in the device of the invention are quite small, even at the pressures of 1 bar (100 kPa) needed to move blood at 1,000 µm/s through the device. An estimate of the gradient can be made by assuming that a tenth of the 4 cm length of the device is constricted by the gap, and, therefore, most of the pressure drop occurs there.

In such a device under those conditions, the average pressure gradient in the gaps is roughly 2 bar/cm, which is on the order of the pressure gradients exerted on blood cells as they traverse the capillaries. Thus, the forces exerted on cells within the device of the invention are not grossly out of the physiological range of hydrostatic forces, and indeed no obvious cell lysis has been observed. The rotation and distortion of compliant objects in the complex vector flow fields of the arrays is a more serious issue that can change the effective critical size, $D_c$. For example, a red blood cell has diameter of about 8 µm, but is only 2 µm thick. As a result, if there is a preferential orientation of the red blood cell in the gap flow pattern at high speeds, there will be a dramatic change in bumping of the red blood cells. Another possibility is that the shear fields at high flows can deform red blood cells into sausage shapes, taco, or parachute shapes.

Devices in accordance with the present invention provide a bimodal separation. For example, in an array, a single region of posts will have a single critical size, and will result in particle flow in two directions. Particles will either travel straight through the array, or will be "bumped" at the angle of the array. Devices of the invention can be designed for the dispersion of particles of different sizes. Such a device may be called a fractionating device. To separate particles according to a range of sizes in a fractionating device, a number of arrays are preferably placed in series, each with a slightly different critical size, $D_c$, in a "chirped" design. The critical size, $D_c$, is a function of the gap size G and the shift fraction $\epsilon$. Either the gap size or the shift fraction can be changed in each successive region to create the desired $D_c$.

Figure 2:
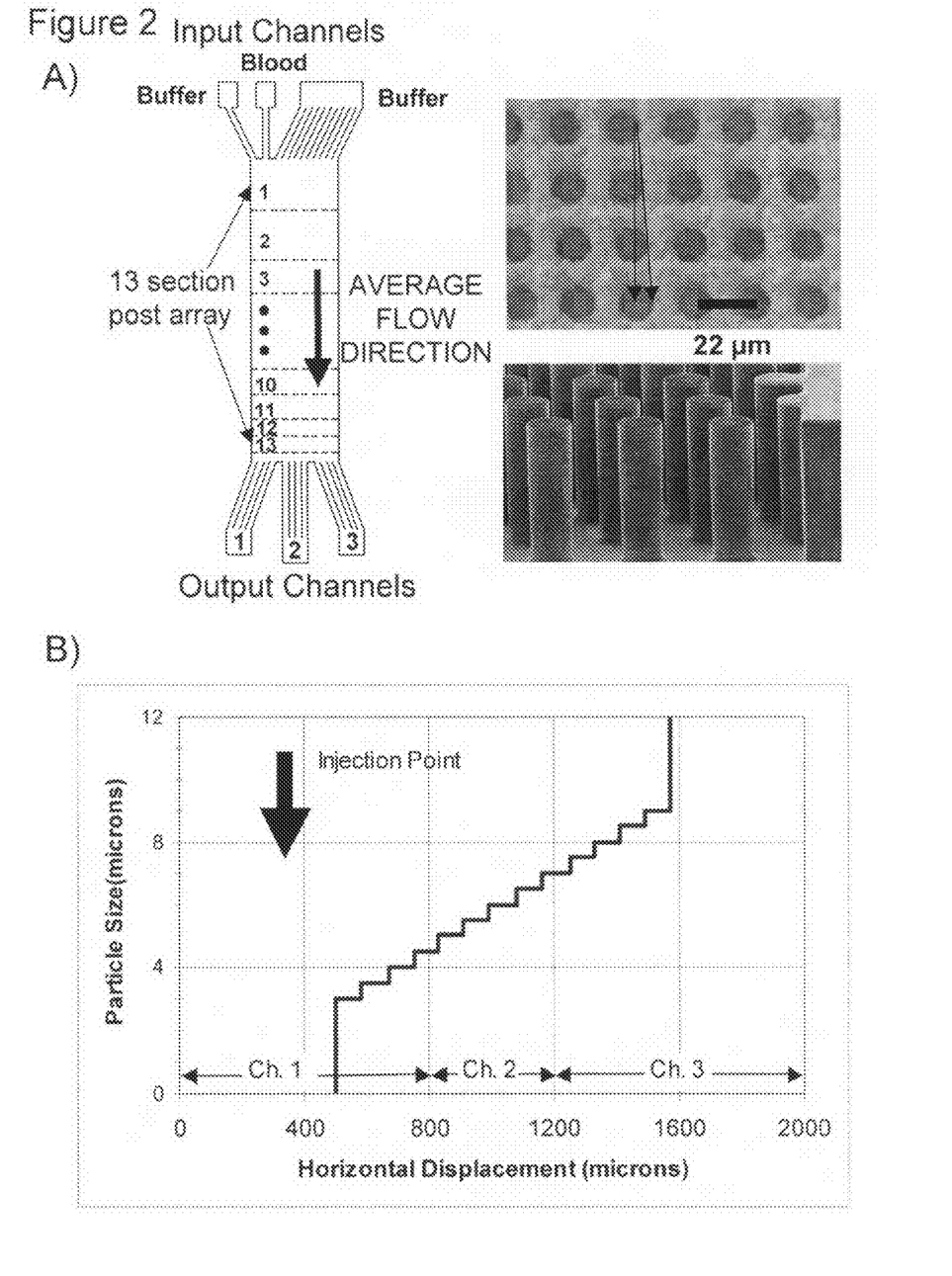
FIG. 2 illustrates a fractionating device (FD) designed to separate white blood cells from other blood components. As illustrated in the left portion of FIG. 2A, the device comprises of 13 functional regions with a fixed gap, G, of 10 μm and a varying λ Microfluidic channels supply buffer and blood at the top, and allow cells to exit at the bottom. The top microphotograph in FIG. 2A shows the top view of the array, with the arrows indicating the vertical and bumping directions, while the lower microphotograph shows a view of posts.

For example, a device having 13 sections was fabricated with a fixed G, while varying $\epsilon$ over the range of 0.04 to 0.4. The critical size for the arrays in the device varied from 3 to 9 µm at 0.5 µm intervals, where the initial arrays had the smaller critical size, and the critical size increased by 0.5 µm in each succeeding array. Such a device is illustrated in FIG. 2. Particles larger than 9 µm were "bumped" in all regions of the device, and those having a size less than 3 µm flowed straight through. Particles having a size in the range of 3 to 9 µm were all "bumped" in the initial section of the device, which had the smallest critical size. Once particles entered an array having a critical size larger than the particle size, the particles were no longer "bumped," and effectively flowed straight through the device.

The dynamic range is an important factor in the evaluation of separation technologies. The term "dynamic range", as used herein, refers to the ratio of size of the largest critical size to that of the smallest critical size that can usefully be achieved within the device. The critical size, $D_c$, can, in principle, be made infinitely small by fabricating an array with a small row shift fraction, $\epsilon$. However, a small shift fraction results in a very low bumping angle, requiring long arrays. In practice, it has been found that that a shift of about G/5, which can be obtained with a value of $\epsilon$ of about 0.02 and bumping angle of 1°, is a preferred minimum in many situations for arrays when its fluid is driven by hydrodynamic pressure. In principle, the critical size can be as large as desired with the use of a large G and $\epsilon$. However, in a chirped array, the largest maximum particle size that can flow without clogging is determined by the smallest gap size. As a result, the preferred maximum dynamic range for a chirped array is on the order of about 3 to 5.

Prior to the present invention, separation or fractionation over a larger range required multiple devices, either cascaded or placed in series. The present invention provides the connection and integration of separation devices in a single planar device, such as a microfluidic chip. As a result, the present invention provides an integrated device that can have a simple input and output structure without requiring complex off-chip fluid handling, as the pressure drop from the input to each of the outputs is the same.

To increase the dynamic range, multiple regions, either chirped or single, can be cascaded successively, where each region has a successively smaller critical size. As used herein, such a device is referred to as a "cascade" design. Cascade devices require an additional feature beyond those of a chirped array. Once larger particles have been separated in one section, they are preferably removed from the active region of the device to prevent clogging of the next section of the device. This removal can be achieved in a number of ways, such as exit channels at the end of each region to remove that portion of the stream that contains the separated large particles. For example, a cascade device having two separate stages can be fabricated, each of which "bumps" large particles to the right, where, at the end of the first stage, the stream at the right with large particles flows to an exit port at atmospheric pressure, and that the end of the second array is at atmospheric pressure as well. The pressure across the bottom of the first array and the top of the second array will not be uniform because of the pressure drop across the second array. This drop will cause the flow on the first and second arrays to not be precisely vertical, especially near the boundary, adversely affecting the device performance. To solve this problem, either the output ports must be held at separate pressures, or some extra fluidic resistance must be added to balance the pressure differentials of the different flow paths and restore vertical flow.

Figure 3:
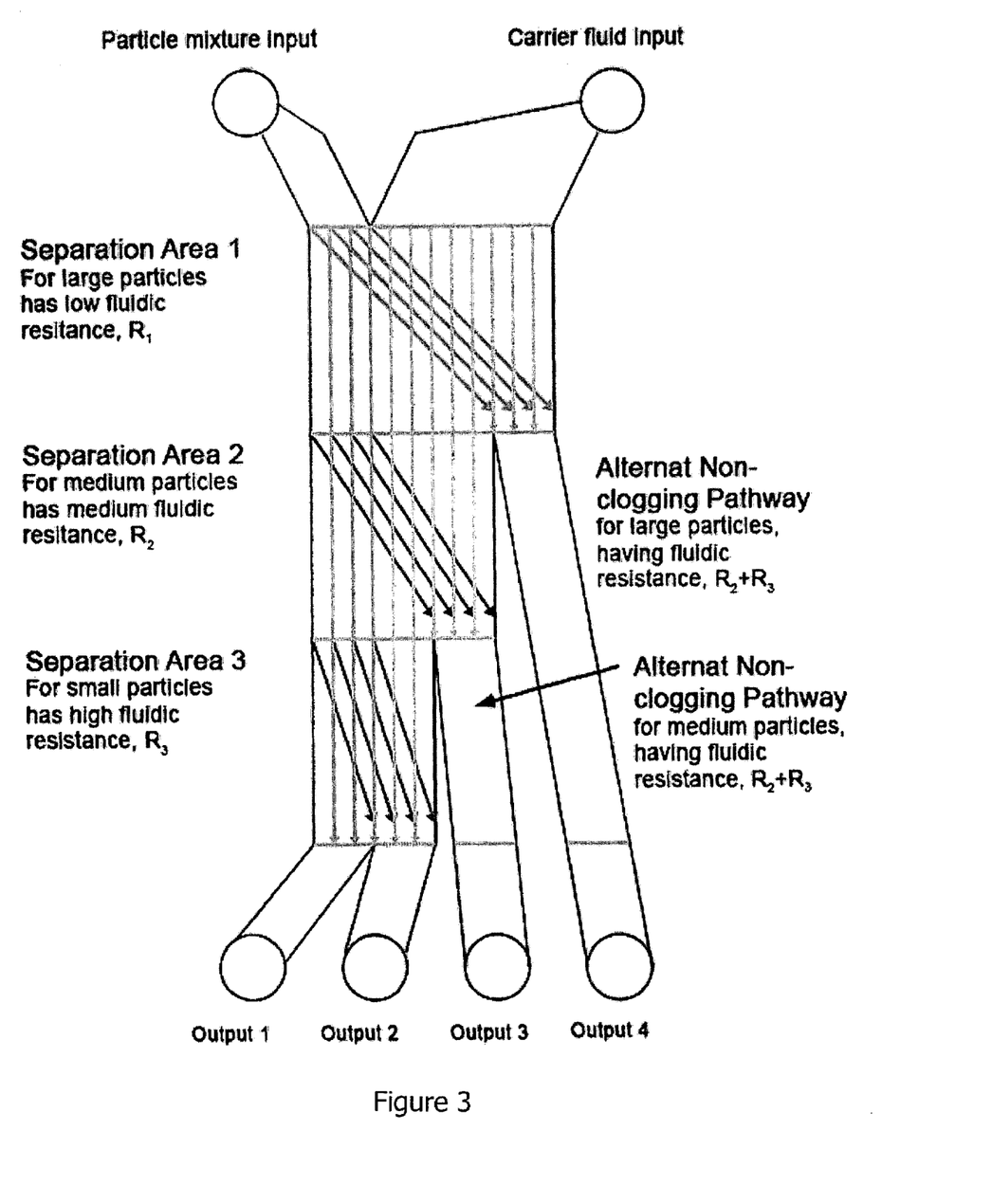
FIG. 3 illustrates a device having three cascaded separation areas, each with a decreasing particle separation range, and alternate non-clogging pathways for particles separated in Areas 1 and 2. The total fluidic resistance of the alternate pathway leading to Output 4 must equal the sum of the fluidic resistance in Separation Areas 2 and 3. The fluidic resistance of the Alternate pathway leading to Output 3 must equal the fluidic resistance of Separation Area 3. As the alternate pathways must have larger gaps than the Separation Areas that they bypass, they must be longer (not shown) than those separation areas to result in equivalent resistance.

Preferably, large, separated objects are removed by providing an alternate, non-clogging pathway for the larger particles to prevent clogging or jamming downstream features, such as those illustrated in FIG. 3. Alternate, non-clogging pathways that do not disturb the flow profile in the separation area are preferably provided by designing alternate pathways with fluidic resistances that are equal to the adjacent or parallel separation areas. This ensures that an equal pressure drop for every possible path through the integrated device. Alternatively, the total length of the device can be shortened by collecting separated cells in a narrow, fast moving, area adjacent to the separation area.

For low Reynolds numbers the fluid velocity at position r(x,y) in a rectangular pipe of dimension (h×l) is:

$$u(x, y) = \left(\frac{4Gh^2}{\mu\pi^3}\right)\sum_{l=0}^{\infty} \frac{(-1)^l}{(2l+1)^3}\left[1 - \frac{\cosh((2l+1)\pi x/h)}{\cosh((2l+1)\pi\omega/2h)}\right]\cos((2l+1)\pi y/h$$

where G is the pressure drop per unit length and µ is the fluid viscosity. This can be rewritten in terms of the fluidic resistance per unit length, R.

$$R = \frac{G}{\int_0^\omega \int_0^h u(x,y) dx dy}$$

When the rectangular channel or pipe becomes tall and narrow, or flat and wide, the resistance per unit length approaches the Hele-Shaw result:

$$R = \frac{12\mu}{h^3 \omega}$$

When the channel is a square the resistance per unit length is very similar to the Poiseuille result for a cylindrical pipe:

$$R = \frac{28\mu}{\pi d^4}$$

Assuming a cylindrical pipe, pipes having a diameter of 5 µm and a length of 100 µm would have the same end to end resistance, i.e., the same volumetric flow rate for a given total pressure drop, as a pipe having a diameter of 10 µm and a length of 1,600 µm and of a pipe having a diameter of 20 µm and a length of 25,600 µm. This provides only two ways to affect the fluidic resistance of a pipe or channel, the diameter or gap and the length. Since the alternate path ways must not clog, they must have a relatively large gap, so these pathways must be longer than the paths through the cascaded separation devices.

The paths, both through the separation devices and the alternate pathways may contain pathways which are significantly more complex than a rectangular pipe. These complex paths include posts or other features that perform the separation, and serpentine like structures that increase, to a limited extent, the resistance of the alternate pathways. In these cases it is necessary to perform numerical simulations using a finite element analysis software package, such as COMSOL Multiphysics (Burlington, Mass.).

Figure 4:
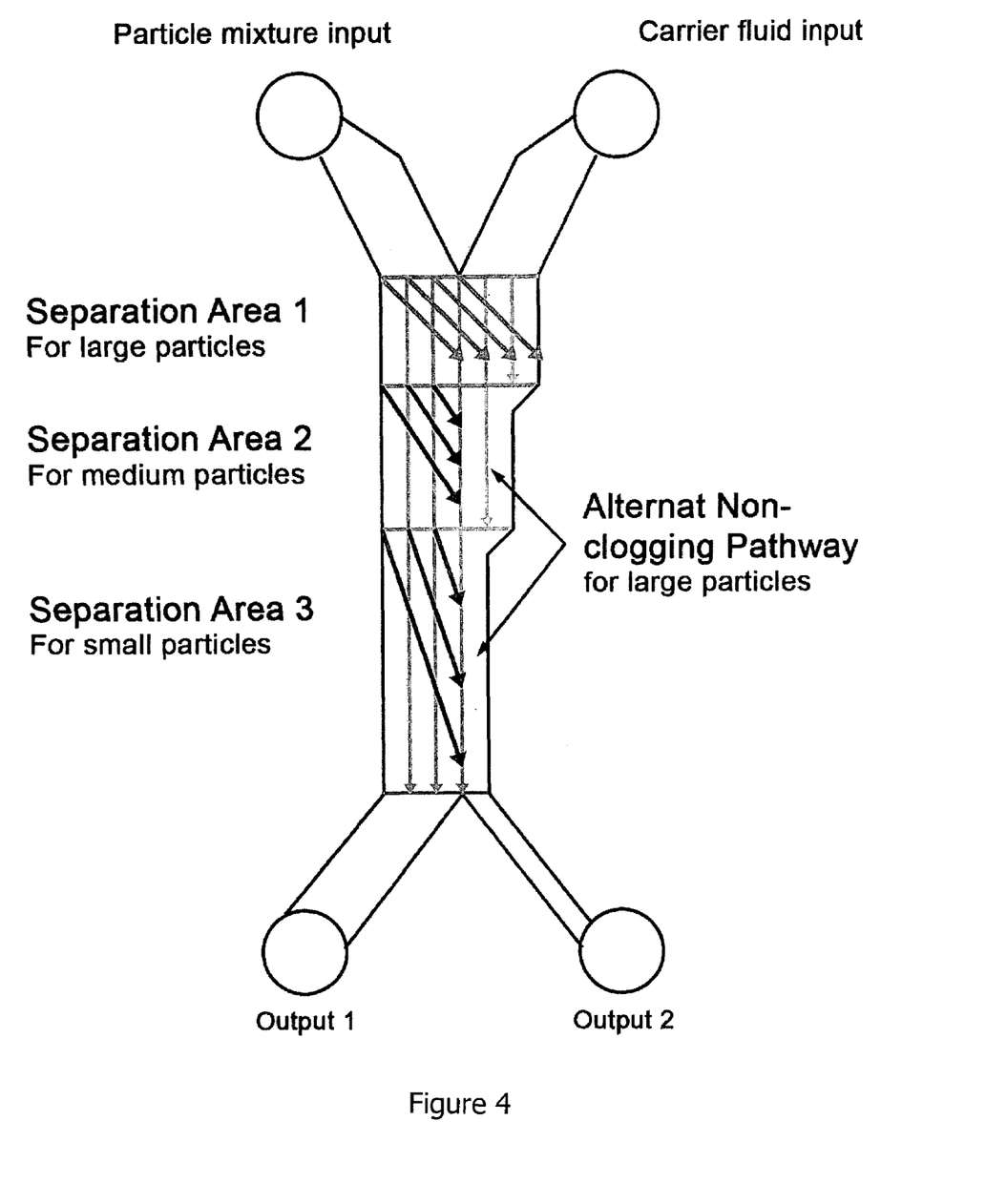
FIG. 4 illustrates a device with three cascaded separation areas, each with a decreasing particle separation range. The alternate non-clogging pathway runs parallel and adjacent to the last two separation regions. This reduces the length of the device. The width of the non-clogging pathway is reduced at each section to increase the speed in the low resistance non-clogging pathway. This ensures vertical flow in the separation areas.
Figure 5:
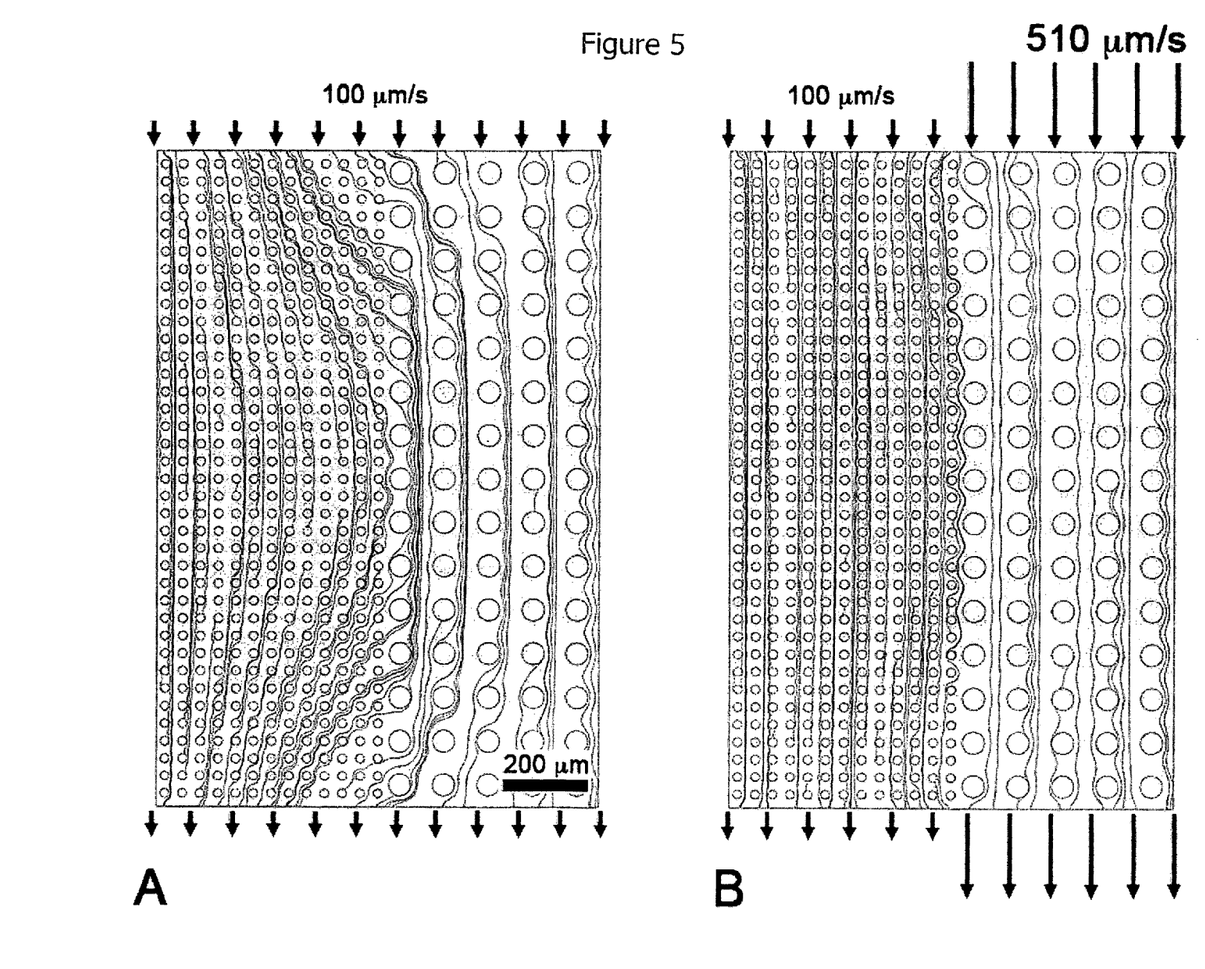
FIG. 5 illustrates the results of two computer models of fluid flow through adjacent high and low resistance post arrays. The circles are the posts, and the lines illustrate the fluid flow around the posts. The darker, heavier lines are lines of flow. The area on the left of A and B has smaller posts and smaller gaps, giving it a higher resistance than the area on the right of A and B.

Continuous separation systems can separate particles at a small angle to the un-separated particles. As illustrated in FIG. 3, particles moving from the left side to the right side in separation areas 1 and 2 require a very long device where the angle is small. A longer microfluidic device has a higher fluidic resistance, and, thus, to attain a certain average flow speed of volumetric throughput, higher pressure is required. The device can be shortened by directing all of the separated particles into output 2, along a parallel and adjacent non-clogging pathway, where there is no boundary between the separation area and the non-clogging pathway, as illustrated in FIG. 4. This non-clogging pathway does not have the same resistance as the adjacent separation area, as it cannot be made any longer than the separation area that runs parallel to it. FIG. 5 illustrates how to maintain the vertical flow profile in the separation area by increasing the flow speed and volumetric throughput through the low resistance non-clogging pathway.

If two fluid carrying regions with different fluidic resistances are placed next to one another, as in FIG. 5A, where equal fluid flux is supplied across the top of the array, fluid from the high resistance region will flow into the low resistance region. It is possible to correct for this by supplying additional fluid flux for the low resistance region, as in FIG. 5B. This provides vertical flow throughout the high resistance separation area.

Control of the incoming and outgoing fluid flux to and from each area is exerted by controlling the width and resistance of upstream and downstream channels. If as shown in FIG. 4, if the fluidic resistance of the alternate pathway adjacent to separation area 2 had two thirds the fluidic resistance of separation area 2, it would require 1.5 times the fluid flux to ensure vertical flow. By narrowing the width of the non-clogging pathway by 1 part in 3, it provides 1.5 times the fluid flux. In separation area 3, the adjacent pathway has one third the resistance of separation area 3. By reducing the width of the alternate pathway by 3, the speed there is increased by a factor of 3, and ensures vertical flow.

Figure 6:
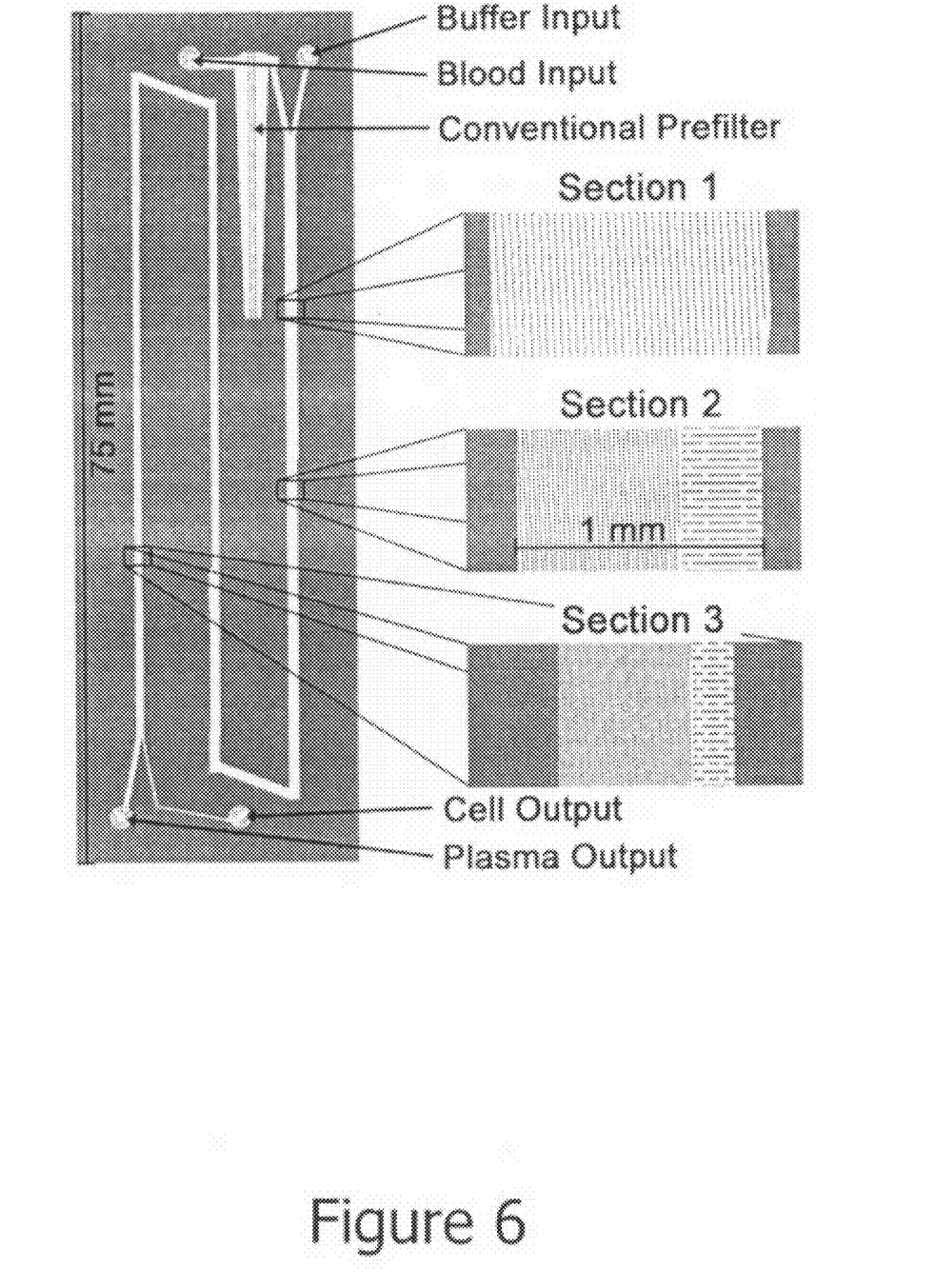
FIG. 6 illustrates a device in which blood flows through three successive arrays to remove cells of decreasing size. Separated blood cells are displaced laterally into the serpentine pattern shown on the right of each section. The serpentine pattern is a non-clogging alternate path that runs adjacent to the separation areas. The pre-filter was designed to remove particles having a size greater than 20 µm.

The invention also provides a plasma separation device that utilizes a cascade design that separates larger cells from successive bumping regions while preventing clogging. Such a device was constructed with three separate regions with gaps of 20, 9, and 5 µm, respectively. The device is illustrated in FIG. 6, and has an additional serpentine pattern on the bumping side of the device, designed to maintain straight laminar flow by matching the fluidic resistance of the array. This region collects the large particles, and prevents them from clogging the successive smaller gaps. With this or similar additions, the cascade design can have a dynamic range of 20 or more.

The operational mode of a device of the invention can also be modified by changing the throat width, W, which is the input width of the injection stream of a sample, such as blood. This throat width can be particularly tailored for particular applications. For example, a small width, on the order of the size of the gap within the device, can be used for small sample volumes and for fractionation analysis with high resolution. A large throat width, on the order of half of the width of the array, allows for large volumes of blood to be flowed, for example, in the removal of cells for plasma preparation.

EXAMPLES

The following non-limiting examples are merely illustrative of the preferred embodiments of the present invention, and are not to be construed as limiting the invention, the scope of which is defined by the appended claims.

The exemplified devices were each constructed on 100 mm silicon wafers, patterned by standard photolithography. The features were etched by using a Bosch silicon etching process to obtain nearly vertical sidewalls. Devices were coated with a fluorosiliane vapor and sealed by glass coverslips coated with polydimethylsiloxane (PDMS) silicone on the sealing surface. Devices were placed into a Plexiglas chuck for loading and application of pressures.

Example 1

Fractionating Device

An analytical fractionating device was fabricated to separate white blood cells from red blood cells and plasma, and to fractionate the white blood cells according to size. The device had a narrow throat width of 50 µm, and was designed to work with 10 µl of blood or less, rather than large volumes. The device is illustrated in FIG. 2. As the main design concern was to create a high dispersion with a range in the sizes of white blood cells of 5 to 10 µm, the device was not designed to remove smaller objects, such as platelets, which have a diameter on the order of 1 µm. Therefore, the required dynamic range was less than 4, and only a single chirped ϵ region with a constant gap G was required. A schematic of the device is illustrated in FIG. 2A.

Whole blood and a running buffer were introduced into separate channels at the top of the device, and vertical laminar flow was maintained throughout the device. The active region of the device had 13 consecutive regions with $D_c$ values of from 3 to 9 µm, created by varying ϵ in the chirped design. Cells separated by "bumping" were passed into the running buffer. The device also had three separate output collection channels, each of which collected a portion of the volume of fluid exiting the device. More than three output channels would have been possible for higher resolution, but three was chosen for ease of the post run analysis. The device was designed to separate cells of slightly differing hydrodynamic radii, and to put those fractionated cells into different output channels.

FIG. 2B graphs the expected horizontal position of cells of different sizes at the end of the device according to the design criteria. Objects of progressively larger hydrodynamic radius were displaced further and further right in each region. Cells behaving as objects larger than the maximum critical size for all 13 regions, i.e., those having a size equivalent to a hard sphere having a diameter greater than 9 µm were, thus, displaced about 1,500 µm from the left edge of the device, placing those particles into channel 3. Particles having a size equivalent to less than that of a hard sphere having diameter of about 3 µm passed straight through the device, and exited through in channel 1. A small number of output channels were chosen so that each channel would yield a reasonable quantity of fluid that could be collected for later external analysis by conventional flow cytometry.

Freshly drawn whole human blood from a finger prick was loaded into the center running well of the device, and running buffer was introduced into the ports on the left and right sides of the specimen port, as illustrated in FIG. 2. Suction was applied to the exit of the device to move the blood through the device. The cells traveled at an average speed of about 1,000 µm/sec under a negative pressure or suction of −0.1 bar, across 1 cm of the array. The throughput of analyzed blood was about 0.3 nl/sec at that pressure gradient.

One microliter of blood was run through the fractionating over a period of 1 hour. The fractionated components were collected at the output of each of the three exit ports. The resulting fractionated components, each having a volume of 50 µl, were removed from each of the exit ports with a pipette. The samples obtained from each exit port were divided in half for separate analysis of red and white blood cells by conventional flow cytometry. To identify white blood cells in the output and differentiate between different white blood cell subpopulations, half of each channel output was stained by using antibodies to the following: CD45 (a generic white blood cell marker, tagged with fluorescent Per-CP), CD19 (a B lymphocyte marker, tagged with phycoerythrin, PE), and CD3 (a T lymphocyte marker, tagged with FITC). All stains were obtained from BD Biosciences (San Diego, Calif.). The mixtures were then lysed with FACSlyze (BD Biosciences) to remove the red blood cells in the white blood cell population.

Figure 7:
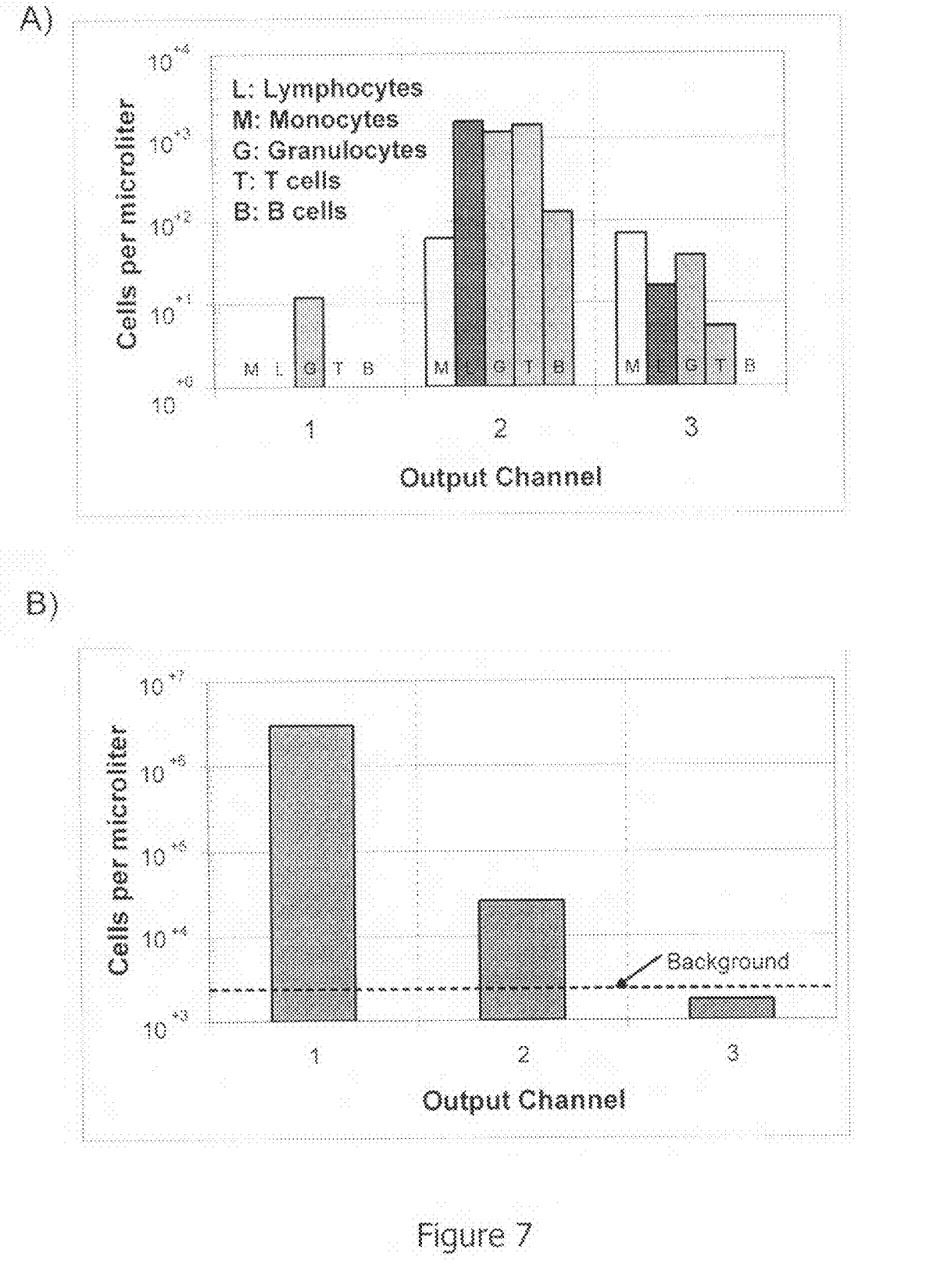
FIG. 7 illustrates white blood cell (A) and red blood cell (B) concentrations in the three output channels of the Fractionation Device of FIG. 2. White blood cells analyzed were lymphocytes, monocytes, granulocytes, B cells, and T cells. Concentrations were measured with flow cytometry and Trucount beads.

The second half of each mixture for the analysis of red blood cells was not lysed. Instead, each set of mixtures was placed into a Trucount test tube (BD Biosciences), which contained a known number of fluorescent beads, to allow calculations of cell concentrations. Each set was analyzed on a FACScan (BD Biosciences) flow cytometer. The conventional flow cytometry analysis of forward scatter, side scatter, and three fluorescent colors was conducted. Lymphocytes, monocytes, and granulocytes were then grouped based on forward and side scatter. Lymphocyte analysis consisted of first gating on CD45 particles with low side scatter, followed by quantification of CD19 and CD3 cells by fluorescence. FIG. 7 shows the cell counts obtained for each type of white and red blood cells. Undisplaced fluid flow from the injection channel exited through output channel 1. One hundred percent of the lymphocytes, monocytes, B cells, and T cells were displaced into channels 2 and 3. Cells displaced between 400 and 800 µm from the undeflected flow, i.e., between 800 and 1,200 µm from the left wall, were preferentially extracted from channel 2, and corresponded to a hard sphere size of from about 4.5 to about 7 µm. Cells displaced 800 to 1,200 µm from the undeflected flow, i.e., between 1,200 and 1,600 µm from the left wall, were preferentially extracted from channel 3, and corresponded to a hard sphere size of from about 7 to about 9 µm. Conventional methods of measuring white blood cells gave an average size larger than 4.5 µm, which agrees with these results. It is also well known that resting lymphocytes are smaller than monocytes by SEM and flow cytometry. For lymphocytes and monocytes, the ratios of the cells in channel 2 to the cells in channel 3 were about 100 to 1 and 1 to 1, respectively. The smaller lymphocytes, on average, were displaced significantly less than the larger monocytes. Most of the lymphocytes behaved like hard spheres having a size smaller than 7 µm. Half of the monocytes were displaced below the 7 µm threshold and the other half above the threshold.

A analysis of granulocytes shows that 100 percent deflection of white blood cells from channel 1 was not achieved. A concentration of about 12 granulocytes per microliter per channel was calculated from the flow cytometry measurements for channel 1, compared to 1,192 for channel 2 and 37 for channel 3. Thus, 99 percent of the granulocytes and 99.6 percent of all white blood cells were displaced into channels 2 and 3. It is not known whether the granulocyte signal in channel 1 represents a real distribution of granulocytes or an ambiguous identification of granulocytes by flow cytometry. Because of the well known tendency of granulocytes to produce a wide range of forward and side scattering intensities, background counts may be incorrectly identified as granulocytes, especially because there is no definitive marker for granulocytes.

The second flow cytometric analysis was designed to measure the number of red blood cells in each output channel. All cells producing forward and side scatter in the flow cytometry were counted as potential cells, except for the Trucount beads, and the expected white blood cells in each channel, based on the lysed blood values, were subtracted to give a raw red blood cell count for each channel, as illustrated in FIG. 7B. A total of $3 \times 10^6$ red blood cells were detected, with 99 percent in channel 1. A flow cytometry analysis of the Trucount beads and the running buffer without blood gave a background concentration of about 2,000 particles per microliter within the forward and side scatter area used for the flow cytometry analysis of white and red blood cells. Thus, the concentration of red blood cells in channel 3, which provided a raw signal of 1,900 particles per microliter, is not significant, and is probably due to this background.

There were a statistically significant number of red blood cells in channel 2, i.e., 26,000 cells per microliter or 0.9 percent of the total red blood cells, which act as hard sphere particles having a size of about 4.5 to about 7 µm. It is not known whether this result is due to a second-order effect, an aberrant red blood cell population, or some other non-ideality. Nevertheless, an enrichment of the white to red blood cell ratio by a factor of greater than 110 from that of the initial blood specimen was obtained from channel 2 of our microfluidic device.

Example 2

Preparative Device

A preparative device was designed and fabricated for the isolation of undiluted blood plasma from whole blood for further study. The device was fabricated with a wide throat width of 500 µm, which was one-half of the 1 mm wide active area. This allowed the preparation of larger volumes and higher flow rates, such that flow rates of at least 1 µl/min were possible, as illustrated in FIG. 6. Because the device was required to remove both large 10 to 20 µm diameter white blood cells as well as small platelets, only the high dynamic range of a cascade device would work without clogging. In the fabricated device, the cascade had three different regions with three different gap sizes. As this particular application required only the production of a substantially cell-free plasma, the individual fractionations produced in each of the regions are not maintained. Instead, all components larger than 1.5 µm were combined in the balanced serpentine region on the side of the device.

FIG. 6 provides a graphical illustration picture of the preparative device. At the top of the illustrated device, whole blood enters the device on the left through a 500 µm wide port, and a running buffer enters the device on the right through a 600 µm wide port. The streams flow parallel to each other, and experience only diffusional mixing, as a result of the low Reynolds number the flowing fluids. The fabricated device had three regions, each with a different gap. The value of $\epsilon$ was 0.040 in the first region for this application, and 0.044 and 0.027 in the second and third regions, respectively. However, it would be easily possible to provide each region with a chirped design if greater resolution was desired. The second and third regions of the cascade each had an additional balanced serpentine region, next to the active region. This serpentine region had a larger minimum size, so that large particles do not clog, allowing the dynamic range to be maintained. To maintain vertical laminar flow, the overall width of the buffer portion was decreased from 600 µm for the first section to 300 µm for the second section and to 160 µm for the third section. As a result, the average vertical fluid velocity in the serpentine region increased by a factor of 2 in the second region, compared to the fluid velocity in the first region, and by a factor of 3 to 4 in the third region compared to the fluid velocity in the first region.

In each region, successively smaller cells were be bumped out of the blood into the parallel stream of buffer. There were two outputs at the end of the device, one to collect the cell-free and undiluted blood plasma and one to collect the cells that had been "bumped" over into the buffer. At the end of all each section, the platelets and red and white blood cells were all traveling in the serpentine pattern within the buffer, while the blood plasma continued to flow on the left of the channel.

Three different blood samples were run in the device. One sample was designed to look at the removal of red and white blood cells from the plasma. It was incubated with Hoechst 33342 to stain the white blood cell nuclei. The red blood cells were observed using white light. The second sample was designed to monitor the more challenging task of the removal of platelets, and was incubated with PE-conjugated CD41 antibodies to specifically label blood platelets, the smallest cells, having a size of about 1 µm, normally occurring in blood. The unbound PE-CD41 was washed out of the sample before running. In this experiment, no platelets were observed in the plasma stream at the end of the device. The third sample was designed to verify the flow of the cell-free plasma. In this case, the unbound PE-CD41 was not washed before the blood was run. The fluorescence of the unbound PE-CD41 in the blood was used to image the flow of the blood plasma. As in the second sample, platelets were easily identified as bright spots, whereas unbound PE-CD41 was identified as a uniformly bright fluorescent background.

Freshly drawn whole human blood from a finger prick was again used. The stained blood was loaded into the left running well, and the running buffer was introduced through a port on the right side of the specimen port. A common pressure was applied to both the blood and buffer ports. At a pressure of 0.3 bar (0.5 pound per square inch), the observed volume of blood flow through the present device was about 0.4 µl/min, with a flow from the top to the bottom of the device. The serpentine region carried cells that had been bumped out of the blood stream. Over the first region, nucleated cells, i.e., white blood cells and a small percentage of red blood cells were observed to travel in the bump mode. Most red blood cells and some platelets were observed to travel in bump mode in the second section, placing these cells in the buffer stream. At the end of section three, the platelets, red blood cells, and white blood cells were all traveling in the serpentine pattern completely within the buffer. The blood plasma continued to flow on the left.

The observation of the intensity of the unbound PE-CD41 dye was important, as that fluorescence intensity came from a molecular species, and tracked the movement of the protein components of plasma. The dye was observed to remain on the left side of the chamber, demonstrating that all of the plasma in the blood can be recovered essentially undiluted by buffer fluid. The unbound fluorescent molecules remained in the blood plasma, and exited the device on the left, free of platelets and cells. The width of the blood plasma stream was less than the width of the incoming blood stream, as half of the volume of the blood is composed of the cells, which had been removed. The device succeeded in removing all blood cell objects having a size of at least 1 µm, including platelets, while maintaining the blood plasma in its undiluted state with essentially 100 percent recovery.

The observed width of the dye stream was not a straight vertical line at the end of the device because of an inadvertent hydrodynamic impedance mismatch between the third section and the output channels. This mismatch caused the plasma stream to widen near the exit. Even before this broadening of the plasma stream at the end due to inadvertent mismatch, the right edge of the dye molecules in the plasma stream near the end of the device were not as sharp as at the top, however. This transition width is about 100 µm, which is consistent with the expected lateral diffusion of the molecules.

Thus, a complex fluid, such as blood, can be separated with the present invention by using a narrow focused hydrodynamic jet to fractionate particles or cells as a function of their diameter in an analytical manner, and by using a broad stream of a preparative sample to remove all of the particles or cells, leaving behind the fluid portion of the sample, which is not been diluted in the process.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:

1. A continuous flow fluidic particle separation device, comprising:
   a sample input;
   a carrier fluid input;
   a plurality of separation areas in fluid connection with the sample input, each separation area configured and adapted to separate particles having a size equal to or greater than a critical size from particles having a size less than the critical size in a flow of a heterogeneous fluid sample through each separation area, the flow having a flow direction, wherein the critical size for each separation area is different, and wherein particles having a size less than the critical size for a separation area and particles having at least the critical size for the separation area move in different directions in the separation area, the particles having a size less than the critical size moving with the flow direction of the fluid sample, and the particles having at least the critical size moving at an angle to the flow direction of the fluid sample;
   at least one non-clogging pathway in fluid connection with the carrier fluid input, configured and adapted to accept separated particles from at least one of the separation areas into a flow of the carrier fluid in the non-clogging pathway;
   a sample output in fluid connection with the separation areas; and
   at least one alternate output in fluid connection with the non-clogging pathway, wherein
   when a heterogeneous fluid sample containing particles to be separated by size is introduced into the device through the sample input, and a carrier fluid is introduced into the device through the carrier fluid input;
   the fluid sample passes through the separation areas;
   the carrier fluid passes through the non-clogging pathway in contact with the fluid sample in the separation areas;
   no mixing other than diffusion occurs between the liquids; and
   particles having at least the critical size separated in each of the separation areas pass into the carrier fluid.

2. The device of claim 1, wherein particles in the heterogeneous fluid sample have a size range of from less than 1 μm to greater than 10 μm.

3. The device of claim 1, wherein particles in the heterogeneous fluid sample have a size range of from less than 1 μm to greater than 20 μm.

4. The device of claim 1, wherein separated particles that pass into the carrier fluid have a size at least that of the critical size.

5. The device of claim 1, further comprising a non-clogging pathway and an alternate output for each separation area, wherein each output has a fluidic resistance that is substantially the same as the other outputs.

6. The device of claim 1, wherein at least one of the separation areas comprises an array comprising a network of gaps within a microfluidic channel.

7. The device of claim 6, wherein the array is an ordered array of obstacles.

8. The device of claim 6, wherein the array is an ordered array of micro- or nano-fabricated features.

9. The device of claim 1, wherein the device has a flow rate of at least about 1000 μm/second.

10. The device of claim 1, wherein the device has a throughput of at least about 1 μl/minute.

11. A method of separating particles by size in a continuous fluid flow, the method comprising:
    introducing a heterogeneous fluid sample into a sample input of a continuous flow fluidic particle separation device, and introducing a carrier fluid into a carrier fluid input of the device, thereby providing a sample flow through a plurality of separation areas and a carrier flow parallel to and in contact with the sample flow, wherein each of the flows has a sufficiently low Reynolds number that there is substantially no turbulence, and mixing of the fluids in the flow occurs only through diffusion;
    separating particles having a size at least that of a predetermined critical size from particles having a size less than the critical size, wherein each separation area has a different critical size, and wherein particles having a size less than the critical size move with the sample flow, and particles having a size at least that of the critical size move at an angle to the sample flow; and
    passing the separated particles into the carrier fluid.

12. The method of claim 11, wherein the fluid sample is blood, and the particles comprise blood cells.

13. The method of claim 11, further comprising separating the particles having a size at least that of the critical size.

14. The method of claim 11, further comprising removing particles separated from a plurality of the separation areas through a single output.

15. The method of claim 11, further comprising removing particles separated in each of the separation areas through separate outputs.

16. The method of claim 11, further comprising removing all particles having a size of at least about 1 μm from the sample fluid in the separation areas.

17. The method of claim 16, wherein the carrier fluid comprises phosphate buffered saline.

18. The method of claim 16, wherein the carrier fluid comprises at least one of an additive that prevents adhesion and anticoagulant.

* * * * *

UNITED STATES PATENT AND TRADEMARK OFFICE
CERTIFICATE OF CORRECTION

PATENT NO. : 7,735,652 B2  
APPLICATION NO. : 11/809559  
DATED : June 15, 2010  
INVENTOR(S) : David William Inglis et al.

Page 1 of 1

It is certified that error appears in the above-identified patent and that said Letters Patent is hereby corrected as shown below:

Specification

Prior to Column 1, line 4, insert the following:

-- GOVERNMENT RIGHTS IN THIS INVENTION
This invention was made with Government support under Grant No. MDA972-00-1-0031 awarded by DARPA (Defense Advanced Research Projects Agency); Grant No. 5 R01 HG001506 awarded by the National Institutes of Health; and National Science Foundation Grant No. ECS-9876771 (Cornell Subaward to Princeton University No. 35399-7459). The Government has certain rights in this invention. --

Signed and Sealed this
Fifth Day of April, 2016

Michelle K. Lee
*Director of the United States Patent and Trademark Office*